United States Patent
Christophersom et al.

(10) Patent No.: US 6,738,671 B2
(45) Date of Patent: May 18, 2004

(54) EXTERNALLY WORN TRANSCEIVER FOR USE WITH AN IMPLANTABLE MEDICAL DEVICE

(75) Inventors: Mark A. Christophersom, Shoreview, MN (US); Adrianus P. Donders, Founex (CH); Keith A. Miesel, St. Paul, MN (US); Len D. Twetan, Excelsior, MN (US)

(73) Assignee: Medtronic, Inc., Minneapolis, MN (US)

( * ) Notice: Subject to any disclaimer, the term of this patent is extended or adjusted under 35 U.S.C. 154(b) by 270 days.

(21) Appl. No.: 10/000,042

(22) Filed: Oct. 26, 2001

(65) Prior Publication Data

US 2002/0123672 A1 Sep. 5, 2002

Related U.S. Application Data

(60) Provisional application No. 60/243,612, filed on Oct. 26, 2000.

(51) Int. Cl.$^7$ .................................................. A61N 1/36
(52) U.S. Cl. ........................ 607/60; 128/903; 128/904; 607/32
(58) Field of Search .................. 600/407, 481, 600/509, 544, 546; 128/903, 904; 607/30, 32, 60

(56) References Cited

U.S. PATENT DOCUMENTS

| | | | |
|---|---|---|---|
| 4,494,950 A | 1/1985 | Fischell | 604/66 |
| 4,622,979 A | 11/1986 | Katchis et al. | 600/515 |
| 4,660,568 A | 4/1987 | Cosman | 600/561 |
| 4,821,723 A | 4/1989 | Baker, Jr. et al. | 607/7 |
| 4,987,897 A | 1/1991 | Funke | 607/32 |
| 5,113,859 A | 5/1992 | Funke | 607/4 |
| 5,113,869 A | 5/1992 | Nappholz et al. | 600/508 |
| 5,131,388 A | 7/1992 | Pless et al. | 607/5 |
| 5,144,949 A | 9/1992 | Olson | 607/17 |
| 5,158,078 A | 10/1992 | Bennett et al. | 607/27 |
| 5,191,891 A | 3/1993 | Righter | 600/523 |
| 5,199,428 A | 4/1993 | Obel et al. | 607/44 |
| 5,207,218 A | 5/1993 | Carpentier et al. | 607/36 |
| 5,289,824 A | 3/1994 | Mills et al. | 600/508 |
| 5,312,453 A | 5/1994 | Shelton et al. | 607/19 |
| 5,314,430 A | 5/1994 | Bardy | 607/5 |
| 5,330,507 A | 7/1994 | Schwartz | 607/14 |
| 5,331,966 A | 7/1994 | Bennett et al. | 600/508 |
| 5,354,316 A | 10/1994 | Keimel | 607/15 |
| 5,511,553 A | 4/1996 | Segalowitz | 600/508 |
| 5,545,186 A | 8/1996 | Olson et al. | 607/14 |
| 5,634,468 A | 6/1997 | Platt et al. | 600/509 |
| 5,683,432 A | 11/1997 | Goedeke et al. | 607/32 |
| 5,720,770 A | 2/1998 | Nappholz et al. | 607/30 |

(List continued on next page.)

FOREIGN PATENT DOCUMENTS

WO  WO 98 33553  8/1998  ............ A61N/1/37

*Primary Examiner*—Carl Layno
(74) *Attorney, Agent, or Firm*—Girma Wolde-Michael; Michael C. Soldner

(57) ABSTRACT

An implantable medical device system that includes an implantable medical device, along with a transceiver device that exchanges data with the patient, between the patient and the implantable medical device, and between a remote location and the implantable medical device. A communication device coupled to the transceiver device exchanges data with the transceiver device, the implantable medical device through the receiver device, and between the transceiver device and the remote location to enable bi-directional data transfer between the patient, the implantable medical device, the transceiver device, and the remote location. A converter unit converts transmission of the data from a first telemetry format to a second telemetry format, and a user interface enables information to be exchanged between the transceiver device and the patient, between the implantable medical device and the patient through the transceiver device, and between the patient and the remote location through the transceiver device.

37 Claims, 8 Drawing Sheets

U.S. PATENT DOCUMENTS

| | | |
|---|---|---|
| 5,721,783 A | 2/1998 | Anderson ................... 381/328 |
| 5,732,074 A | 3/1998 | Spaur et al. ................ 370/313 |
| 5,743,267 A * | 4/1998 | Nikolic et al. .............. 600/483 |
| 5,759,199 A | 6/1998 | Snell et al. ................... 607/60 |
| 5,810,747 A | 9/1998 | Brudny et al. .............. 600/595 |
| 5,833,603 A | 11/1998 | Kovacs et al. .............. 600/317 |
| 5,904,708 A | 5/1999 | Goedeke ..................... 607/18 |
| 5,987,519 A | 11/1999 | Peifer et al. ................ 709/230 |
| 6,082,367 A | 7/2000 | Greeninger et al. ........ 128/899 |
| 6,083,248 A | 7/2000 | Thompson ................... 607/30 |
| 6,115,636 A | 9/2000 | Ryan ........................... 607/60 |
| 6,200,265 B1 | 3/2001 | Walsh et al. ................ 600/300 |
| 6,402,689 B1 * | 6/2002 | Scarantino et al. ......... 600/300 |
| 6,434,429 B1 * | 8/2002 | Kraus et al. .................. 607/60 |
| 6,497,655 B1 * | 12/2002 | Linberg et al. ............. 600/300 |

\* cited by examiner

EXTERNALLY WORN TRANSCEIVER FOR USE WITH AN IMPLANTABLE MEDICAL DEVICE

RELATED APPLICATIONS

This application claims priority and other benefits from U.S. Provisional Patent Application Serial No. 60/243,612, filed Oct. 26, 2000, entitled "EXTERNALLY WORN TRANSPONDER/SENSOR FOR USE WITH AN IMPLANTABLE MEDICAL DEVICE"

FIELD OF THE INVENTION

The present invention generally relates to implantable medical devices and communication therewith, and in particular, the present invention relates to a transceiver device in proximity to the implantable medical device and an external sensor that cooperates with the implantable medical device to produce a desired therapy in one or more implantable medical devices.

BACKGROUND OF THE INVENTION

Various medical devices have been developed that acquire information from one or more physiologic sensors or transducers. A typical physiologic sensor transduces a measurable parameter of the human body, such as blood pressure, electrical activity (ECG), temperature or oxygen saturation, for example, into corresponding electrical signals. In many implantable medical device applications, it is often desirable or necessary to acquire physiological data for extended periods of time and on a continuous basis. In addition to the continuous acquisition of physiological data, there are many applications in which it is often desirable to implement a patient diary of sorts by enabling the patient to input relevant information at appropriate times so that the combined continuous data acquisition and patient input provides a record that can be used to better understand other physiologic events or to create signals.

A problem well known to designers of implantable medical devices, such as pacemakers, for example, concerns the necessity of using low power components, including low power memory and processing components, within the implantable medical device. Use of low powered components is considered necessary in order to provide for extended periods of implantable medical device operation, and to reduce the need to repeatedly replace batteries, which can only be accomplished through surgical means. As a consequence, conventional implantable medical devices typically employ low voltage, low current memory and processing devices, which have limited storage capacity and access speed, and often lag behind the state-of-the-art memory and processing technology by several years. These and other limitations significantly decrease the data storage, processing power, and access capability of implantable medical devices, and often precludes the opportunity to integrate high capacity, low cost, state-of-the-art memory and processing devices in implantable medical device designs.

Various implementations of portable or user-worn electrocardiographic recording/monitoring devices are known in the art, examples of which may be found in the issued patents list in Table 1 below.

TABLE 1

| U.S. Pat. No. | Inventor(s) | Issue Date |
|---|---|---|
| 6,200,265 | Walsh et al. | Mar. 13, 2001 |
| 5,833,603 | Kovacs et al. | Nov. 10, 1998 |
| 5,721,783 | Anderson | Feb. 24, 1998 |
| 5,720,770 | Nappholz et al. | Feb. 24, 1998 |
| 5,759,199 | Snell et al. | Jun. 2, 1998 |
| 5,634,468 | Platt et al. | Jun. 3, 1997 |
| 5,511,553 | Segalowitz | Apr. 30, 1996 |
| 5,289,824 | Mills et al. | Mar. 1, 1994 |
| 5,191,891 | Righter | Mar. 9, 1993 |
| 5,113,869 | Nappholz et al. | May 19, 1992 |
| 4,660,568 | Cosman | Apr. 28, 1987 |
| 4,622,979 | Katchis et al. | Nov. 18, 1986 |
| 4,494,950 | Fischell | Jan. 22, 1985 |

Conventional portable or patient-worn electrocardiographic (ECG) monitor/recorders, such as those disclosed in one or more of the patents listed in Table 1 above, are autonomous systems that enable only limited interaction between the patient and the device, and can only be used in accordance with a single specific telemetry format. Accordingly, what is needed is a device for communicating with an implantable medical device that allows increased patient interaction with the device, seamless transmission of data to other devices, including an Internet appliance, a cellular network, and so forth, enabling use across multiple telemetry formats and between multiple implantable medical devices to store and manage information from a broad range of devices.

SUMMARY OF THE INVENTION

The present invention relates to an implantable medical device system that includes an implantable medical device for implantation within a patient that monitors physiologic conditions of the patient and/or delivers a therapy in response to physiologic conditions. A transceiver device coupled to the implantable medical device along a wireless link exchanges data with the patient, between the patient and the implantable medical device, and between a remote location and the implantable medical device. A communication device coupled to the transceiver device along a wireless link exchanges data with the transceiver device and with the implantable medical device through the transceiver device, and exchanges data between the transceiver device and the remote location. In this way, the implantable medical device system enables bi-directional data transfer between the patient, the implantable medical device, the transceiver device, the communication device, and the remote location.

According to a preferred embodiment of the present invention, a patient wearable transceiver device exchanges data with an implantable medical device for implantation within a patient. The transceiver device includes means for receiving information from the implantable medical device, means for exchanging data between the patient, the implantable medical device, the communication device, and a remote location, and means for processing the data exchanged. The means for receiving, the means for exchanging, and the means for processing enable bi-directional data transfer between the patient, the implantable medical device, the transceiver device, and the remote location.

Another aspect of the present invention includes a converter unit that converts transmission of the data between the implantable medical device, the transceiver device, and the communication device from a first telemetry format to a second telemetry format.

In yet another aspect of the present invention, an implantable medical device system includes an implantable medical device for implantation within a patient that monitors physiologic conditions of the patient, and/or delivers a therapy in response to the physiologic conditions, along with a transceiver device coupled to the implantable medical device along a wireless link that exchanges data with the patient, between the patient and the implantable medical device, and between a remote location and the implantable medical device. A communication device coupled along a wireless link to the transceiver device exchanges data with the transceiver device and with the implantable medical device through the transceiver device, and exchanges data between the transceiver device and the remote location. A converter unit converts transmission of the data between the implantable medical device, the transceiver device, and the communication device from a first telemetry format to a second telemetry format, and a direct interface couples the transceiver device to an external device to enable direct downloading of the data and configuration/setup information to the external device, and connection to user interface devices. An external reference sensor senses a parameter external to the patient, and the transceiver device receives the sensed parameter from the external reference sensor and/or receives data from the implantable medical device. A user interface enables information to be exchanged between the transceiver device and the patient, between the implantable medical device and the patient through the transceiver device, and between the patient and the remote location.

According to yet another aspect of the present invention, the user interface includes a patient physiologic parameter portion that displays the physiologic conditions of the patient, a daily activity diary portion that enables the patient to input activities to the transceiver device, and a medication reminder portion that displays medication reminders in response to a request received from the implantable medical device and in response to data processed by the implantable medical device and the transceiver device. An event storage portion stores information, including the input activities and the physiologic signals associated with the patient, processes the information, and acquires high resolution activity in response to the information. A send message portion stores messages transmitted between the remote location and the transceiver device and/or the patient, and a status portion adjusts and displays battery status, therapy status, and settings of the transceiver device. Finally, a receive message portion of the interface receives messages transmitted between the remote location and the transceiver device and/or the patient, including automated information, adjusting parameters and output of the implantable medical device, along with manual information, input directly at the transceiver device.

According to yet another aspect of the present invention, the data received by transceiver device is used as feedback control information for a second implantable medical device for implantation within the patient.

According to another aspect of the present invention, a removable memory stores information received directly from the transceiver device and received from the implantable medical device through the transceiver device.

According to another aspect of the present invention, the transceiver device triggers the implantable medical device to change from a normal state, in which implantable medical device gathers data at a first rate and performs a relatively high amount of averaging, to a second state in which the amount and resolution of data is increased so that an increased resolution of data is obtained and stored in transceiver device in response to an input to the transceiver by the patient.

BRIEF DESCRIPTION OF THE DRAWINGS

The features of the present invention which are believed to be novel are set forth with particularity in the appended claims. The invention, together with further objects and advantages thereof, may best be understood by making reference to the following description, taken in conjunction with the accompanying drawings, in the several figures of which like reference numerals identify like elements, and wherein:

DETAILED DESCRIPTION OF THE PREFERRED EMBODIMENT

Figure 1:
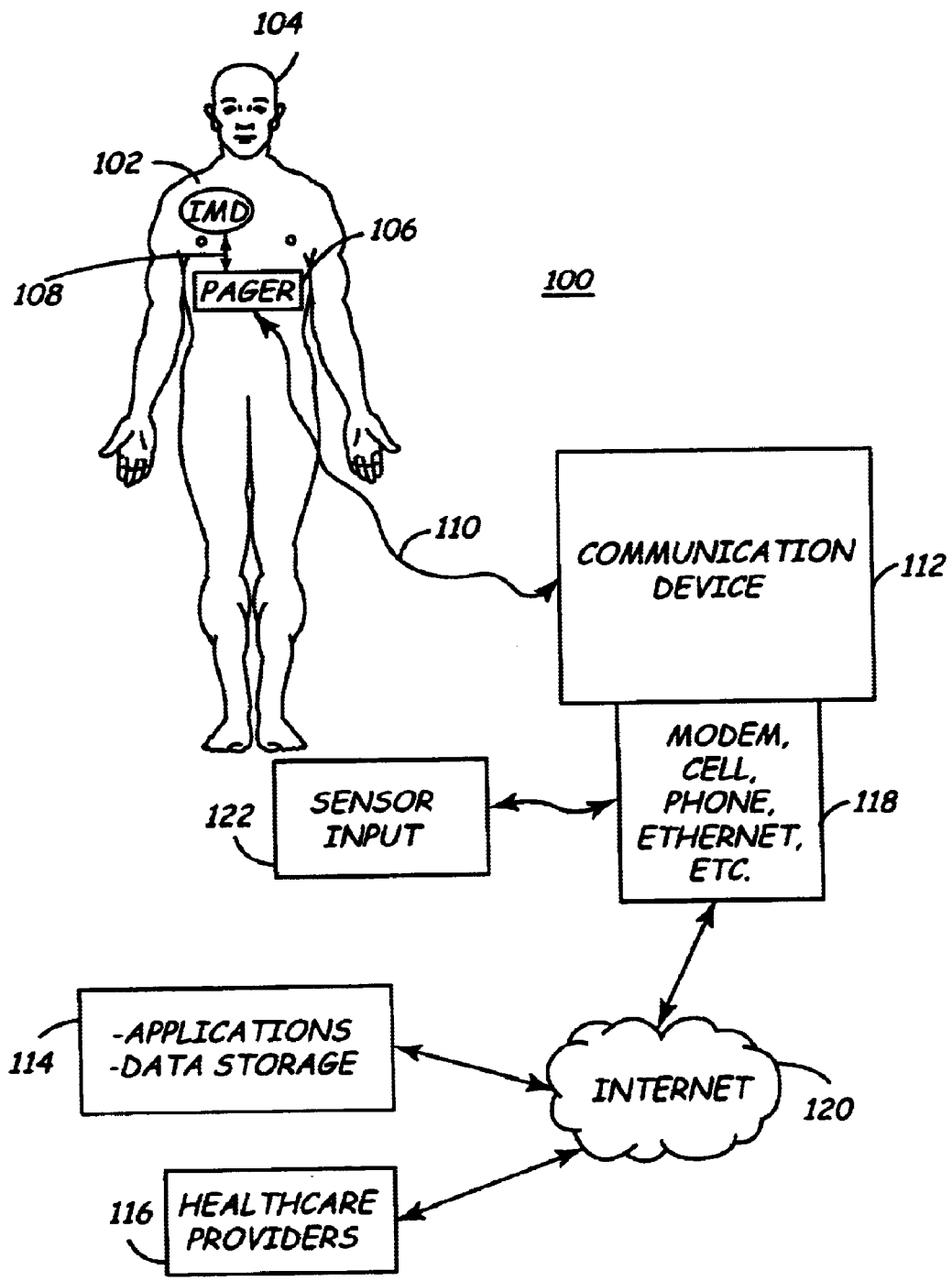
FIG. 1 is a schematic view of an implantable medical device system according to the present invention.

FIG. 1 is a schematic view of an implantable medical device system according to the present invention. As illustrated in FIG. 1, an implantable medical device system 100 according to the present invention includes an implantable medical device 102 implanted within a patient 104 for delivering a therapy in response to physiological conditions of patient 104, or for monitoring conditions of patient 104. Implantable medical device 102 may be an implantable cardiac pacemaker, such as those disclosed, for example, in U.S. Pat. No. 5,158,078 to Bennett et al., U.S. Pat. No. 5,312,453 to Shelton et al., or U.S. Pat. No. 5,144,949 to Olson, hereby incorporated herein by reference in their respective entireties. Implantable medical device 102 may also be a pacemaker/cardioverter/defibrillator (PCD), such as those disclosed, for example, in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties.

Alternately, implantable medical device 102 may be an implantable nerve stimulator or muscle stimulator, such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device, such as the device described in U.S. Pat. No. 5,331,966 issued to Bennet et al., all of which are hereby incorporated herein by reference in their respective entireties. By way of further example, implantable medical device 102 may be an implantable nerve stimulator or muscle stimulator, such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device, such as that disclosed in U.S. Pat. No. 5,331,966 issued to Bennet et al., all of which are hereby incorporated herein by reference in their respective entireties. Implantable medical device 102 may also be an implantable blood oxygen sensing monitor or an implantable hemodynamic monitor.

According to the present invention, implantable medical device 102 monitors any number, combination or type of parameters, such as oxygen, pressure, cardiac flow, stroke volume, cardiac EGM, cardiac acceleration, etc. While implantable medical device 102 has been described as being one of the above-referenced devices, it is understood that the present invention is applicable in any form of implantable medical device requiring storage of appreciable amounts of physiologic, diagnostic, system, or other data, particularly those that acquire information on a continuous or near continuous basis.

In addition, according to the present invention, a transceiver device 106, such as a pager, band-aid, wristwatch, or pendant type device, is worn by, attached to, or positioned within close proximity to patient 104 in order to be bi-directionally coupled to implantable medical device 102 along a wireless telemetry link 108. Telemetry link 108 will be dependent upon the type of implantable medical device utilized. For example, in a medium range system, telemetry link 108 will typically range from approximately 0.1 to 1.0 meters.

Transceiver device 106 is also coupled, along a wireless link 110, such as a RF (UHF) link or an infrared (Ir) link, for example, to a communication device 112, located near or within the patient's home. According to the present invention, communication device 112 includes a base station, a monitor, a physician programmer, or other similar device and is connected to the Internet 120 through a transmission medium 118, such as a modem, cell phone, or Ethernet, etc. In this way, transceiver device 106 exchanges data with a remotely located applications and data storage unit 114, or a remotely located health care provider 116 through transmission medium 118.

Link 110 will be dependent upon the transmission limitations designed for transceiver device 106 and communication device 112, and in a preferred embodiment of the present invention ranges from approximately 1.0 to 100 meters, for example. An additional input or sensor 122 inputs information external to patient 104, such as barometric pressure, temperature, patient body position, and patient posture, for example, to communication device 112. In this way, by enabling bi-directional transmission of data between implantable medical device 102 and remote locations, such as data storage unit 114 or health care provider 116, for example, and between patient 104 and implantable medical device 102, the present invention enables a more seamless method for controlling therapy associated with implantable medical device 102, transmitting data physiologic data remotely back to the physician, in real time, closing a loop between multiple implantable devices, and providing additional processing power in order to perform algorithms externally from implantable medical device 102, as will be described below.

Figure 2:
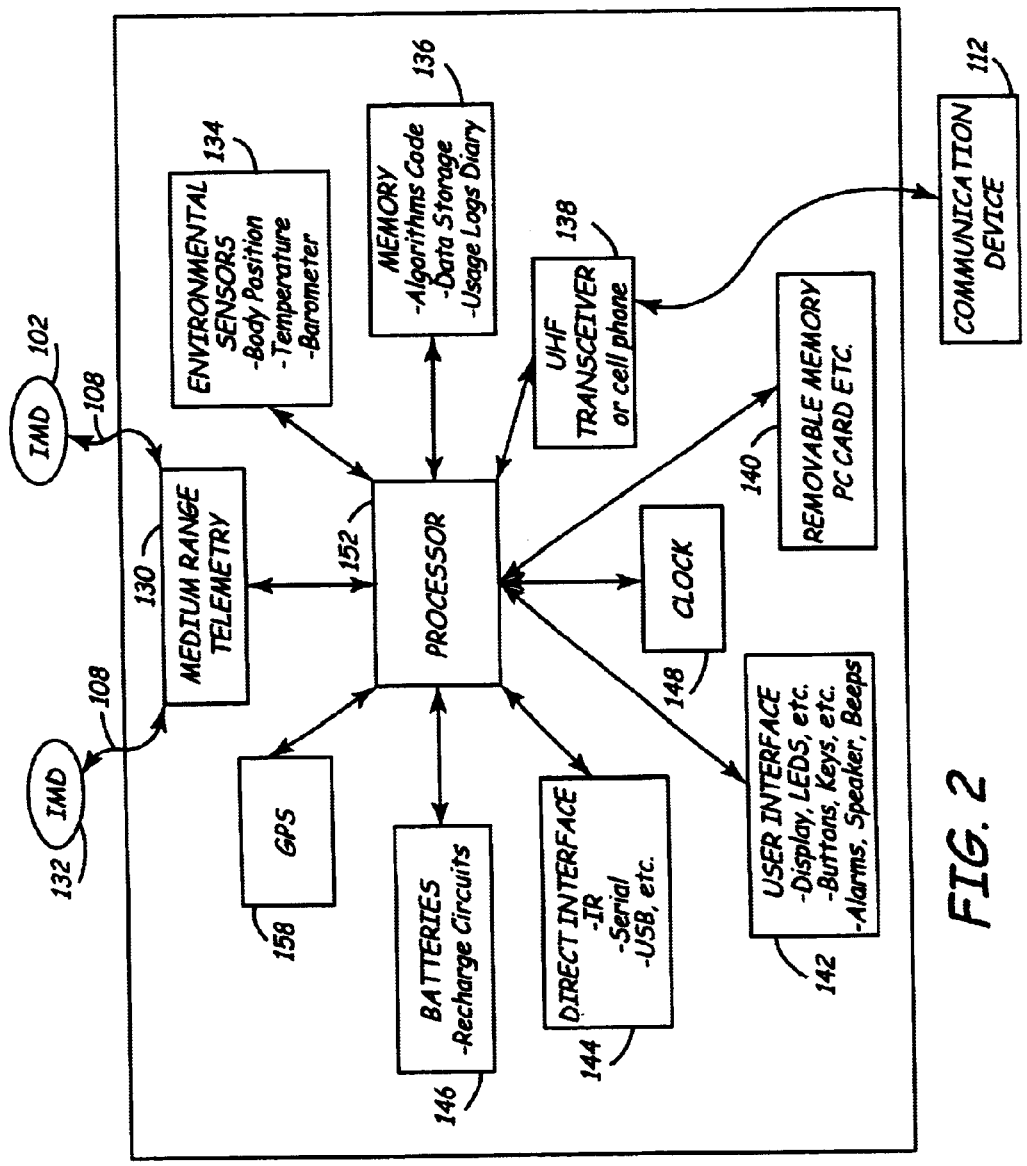
FIG. 2 is a schematic diagram of a transceiver device of the implantable medical device system of FIG. 1 according to the present invention.

FIG. 2 is a schematic diagram of a transceiver device of the implantable medical device system of FIG. 1 according to the present invention. As illustrated in FIG. 2, transceiver device 106 includes a medium range telemetry unit 130 for enabling bi-directional transmission of data between transceiver device 106 and implantable medical device 102. In addition, in situations where a second implantable medical device 132 is located within patient 104, transceiver device 106 of the present invention performs bi-directional data transmission with either one or both of implantable medical devices 102 and 132. An environmental sensor unit 134 includes sensors for determining environmental conditions such as body position of patient 104, temperature, or barometric pressure. A memory unit 136 is utilized to store code and algorithms, in addition to data and usage storage log and directories. A transceiver unit 138 enables the transmission of data between transceiver device 106 and communication device 112 for seamless transmission to remote locations over the Internet. A removable memory 140, such as a PG card, etc., located within transceiver device 106 enables information received either directly from transceiver device 106 or from implantable medical device 102 through transceiver device 106 to be stored thereon. Once the information is stored, removable memory 140 may then be removed from transceiver device 106 and transferred by patient 104 to a physician or other medical personnel, such as when patient 104 does not have Internet connectivity, for example.

According to the present invention, patient 104 inputs information to transceiver device 106 through buttons, keys, etc., located at a user interface 142 of transceiver device 106. In addition, user interface 142 includes a display, LEDs and so forth, along with one or more alarms and speakers, for example, to enable information to be transmitted directly from transceiver device 106 to patient 104, or from implantable medical device 102 to patient 104 through transceiver device 106, and to enable a manual or automated message to be transmitted from the remote location 114 and 116 to the patient. A direct interface 144, such as an infrared port, a serial port, or a universal serial bus connects transceiver device 106 to an external device, such as a laptop, for example, to enable direct downloading of data, configuration/setup information, connection to user interlace devices, and so forth. A power source 146, including one or more rechargeable batteries for example, along with recharge circuitry to power transceiver device 106, is included within transceiver device 106, along with a clock 148, which time stamps all data flowing within transceiver device 106 to correlate when certain events are taking place. A GPS unit 150 located within transceiver device 106 enables the position of transceiver device 106, and therefore the position of patient 104, to be determined when necessary. Finally, a processor 152 located within transceiver device 106 exchanges information with each of devices 130–150, controls therapy associated with implantable medical device 102, controls transmission of data between implantable medical device 102 and a remote location, such as data storage unit 114 or a health care provider 116, provides real time data that can be transmitted from patient 104 to the remote location, including a physician for example, closes a loop between multiple implantable devices, and provides processing power external to implantable medical device 102.

Figure 3:
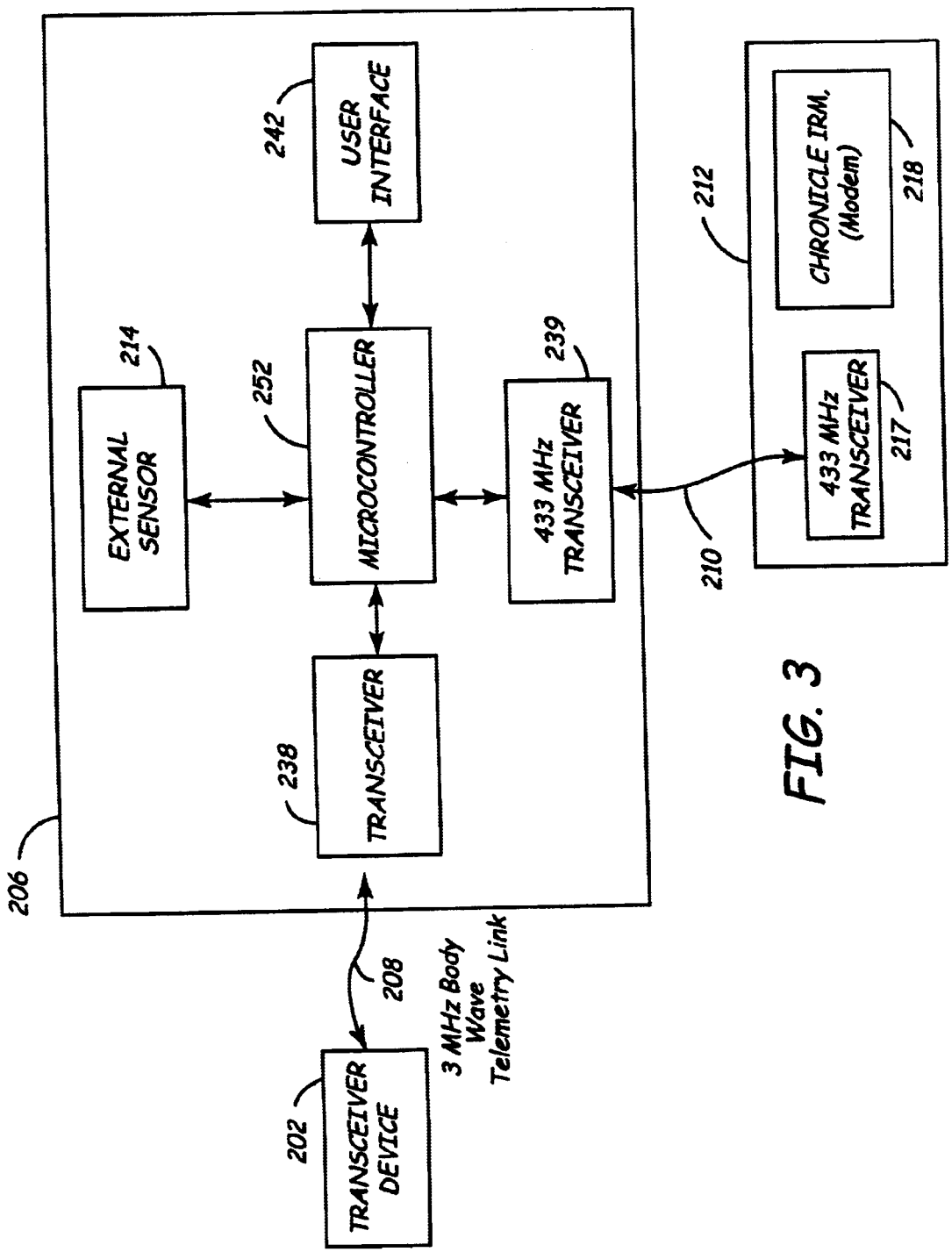
FIG. 3 is a schematic diagram of multi-directional data transmission using a transceiver device of the implantable medical device system of FIG. 1.

FIG. 3 is a schematic diagram of multi-directional data transmission using a transceiver device of the implantable medical device system of FIG. 1. As illustrated in FIG. 3, according to multi-directional data flow transmission of the present invention, an implantable medical device 202, such as the Medtronic Inc. Chronicle IHM with medium range telemetry, for example, exchanges data with a transceiver device 206 along a link 208 between implantable medical device 202 and a transceiver 238. Transceiver device 206 includes a pager type device, for example, positioned within close proximity to, or worn on a belt of the patient, or a band-aid, wristwatch, or pendant type device positioned within close proximity of the patient. Link 208 is a 3 Mhz body wave telemetry link, for example.

An external reference sensor 214 senses a parameter external to the patient, such as barometric pressure, for example. It is understood that, while sensor 214 is described in FIG. 3 as being a barometric pressure sensor, according to the present invention, sensor 214 could sense any parameter external to the patient, such as temperature, position of the patients body, patient posture activity, and so forth. Transceiver device 206 exchanges information with a communication device 212 along a wireless link 210 between a transceiver 239 of transceiver device 206 and a transceiver 217 located within communication device 212. Link 210 is, for example, a 433 MHz radio frequency (RF) link having a range of approximately 10 to 30 meters. Communication device 212, which according to the present invention includes a base station, a monitor, a programmer or similar device, in turn exchanges information with a remote location, such as data storage unit 114 or a health care provider 116 (FIG. 1) through a modem 218 and the Internet 120.

A user interface 242 is similar to interface 142 of FIG. 2, and includes an LCD, audible tones and input buttons to enable the patient to input information within transceiver device 206 at any time, so that the present invention provides the patient with an increased level of control over their health and/or therapy. For example, according to the present invention, during an initial visit, a physician may instruct the patient to ingest a certain drug if the patient's heart rate reaches a certain level or if the patient's blood pressure reaches a certain level so that once the patient's heart rate or blood pressure is subsequently displayed on LCD of interface 242 as being above the prescribed level, the patient is able to act accordingly on their own.

In addition, according to the present invention, once the heart rate or blood pressure reaches the prescribed level, an audible alarm sounds from interface 242 to inform the patient of the status of the parameter. Likewise, according to the present invention, information and instructions can be communicated from the remote location to the patient through transceiver device 206 and communication device 212. For example, the physician at remote location 116 (FIG. 1) transmits reminders or requests for the patient to visit the physician, directions to remote location 116, and so forth, or manual or automated messages are transmitted from the physician, which are displayed to the patient at user interface 242, or transmitted to the patient using audible tones of interface 242. Battery levels, drug levels of drug pumps, and information regarding other type of therapies that the patient is currently on are also displayed at interface 242. In addition, medication reminders, which are displayed or audibly transmitted at interface 242, are changed or updated at remote location 114 and 116, so that when, as a result of data remotely received and conversations held between the physician and the patient, a need to change medication levels is identified, the physician is able to download the change directly within transceiver device 206 and the reminder schedule would be updated.

In addition, transceiver device 206 of the present invention enables the patient, during a heart palpitation, for example, or other such event, to activate an input at interface 242 to store detailed therapy status or physiologic signals regarding the event. Once informed of the event, transceiver device 206 triggers implantable device 202 to change from a normal state, in which implantable medical device 202 gathers data at a slow rate, or not at all, and performs a relatively high amount of averaging, to an increased state in which the amount and resolution of data is increased, so that a higher resolution of data can be obtained and stored in transceiver device 206, concurrent with the onset of the event, which can then be utilized in future diagnosis by the physician.

In addition, as illustrated in FIG. 3, microcontroller 252 of transceiver device 206 receives and correlates raw pressure data received from sensor 214 to atmospheric pressure and determines, using the correlated data and a predetermined algorithm, whether drug dosages should be increased or decreased or whether a closed loop drug or other therapy (electrical pacing, etc.) should take place. This determination is then transmitted along link 208 to implantable medical device 202 or to remote location 114 and 116 (FIG. 1), which responds accordingly. For example, in a situation where implantable medical device 202 is a drug delivery device, implantable medical device 202 adjusts dosage amounts accordingly, or where an implantable medical device 202 is an implantable cardiac pacemaker, implantable medical device 202 increases the pacing rate of the patient either automatically, or in response to input received from a physician located at a remote location, such as health care provider 116, through communication device 212 and transceiver device 206.

Figure 4:
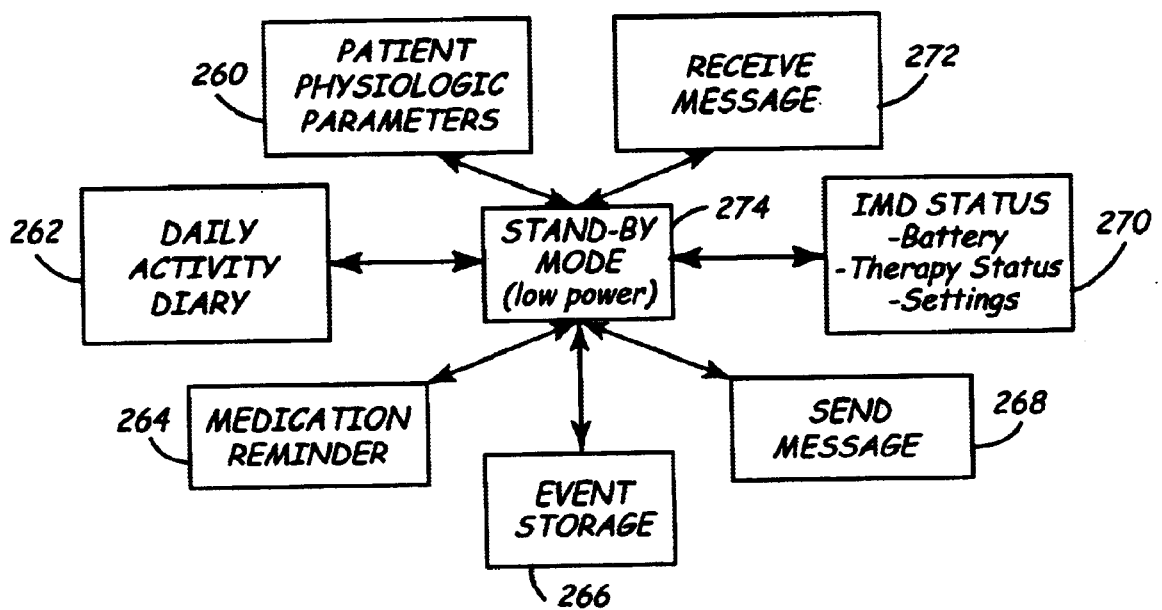
FIG. 4 is a schematic diagram of a user interface of a transceiver device of the implantable medical device system of FIG. 1.

FIG. 4 is a schematic diagram of a user interface of a transceiver device of the implantable medical device system of FIG. 1. As illustrated in FIGS. 3 and 4, interface 242 of the present invention includes a patient physiologic parameter portion 260 that displays physiologic data of the patient, such the patient's heart rate, blood pressure, and so forth, and a daily activity diary portion 262 that enables the patient to enter activities such as eating activity, sleeping activity, exercise activity, restroom visits, and so forth. A medication reminder portion 264 uses clock 148 (FIG. 2) to display medication reminders, or displays reminders in response to a request received by transceiver device 206 from implantable medical device 202, and/or in response to data processed by implantable medical device 202 and transceiver device 206. An event storage portion 266 stores physiologic signals associated with the patient, processes signals, acquires the high resolution signal activity, and so forth, while a send message portion 268 stores messages transmitted between the remote location 116 and transceiver device 206 and/or the patient, such as a data snap shot, text messages from the physician, an event trigger, such as a tachycardia or bradycardia event, and so forth. An implantable medical device status portion 270 adjusts and/displays battery status, therapy status, and device settings, while a receive message portion 272 stores messages transmitted between remote location 114 and transceiver device 206 and/or the patient, such as automated information that adjusts parameters or output of implantable medical device 202, or manual information input directly at transceiver device 206. As illustrated in FIGS. 3 and 4, in a low power standby mode 274, transceiver device 206 powers circuits that are not required, such as those associated with portions 260–272 of interface 242. While in standby mode 274, transceiver device 206 periodically "listens" for signals from either implantable medical device 202 or communication device 212 to transition from standby mode 274 to an active mode.

Figure 5:
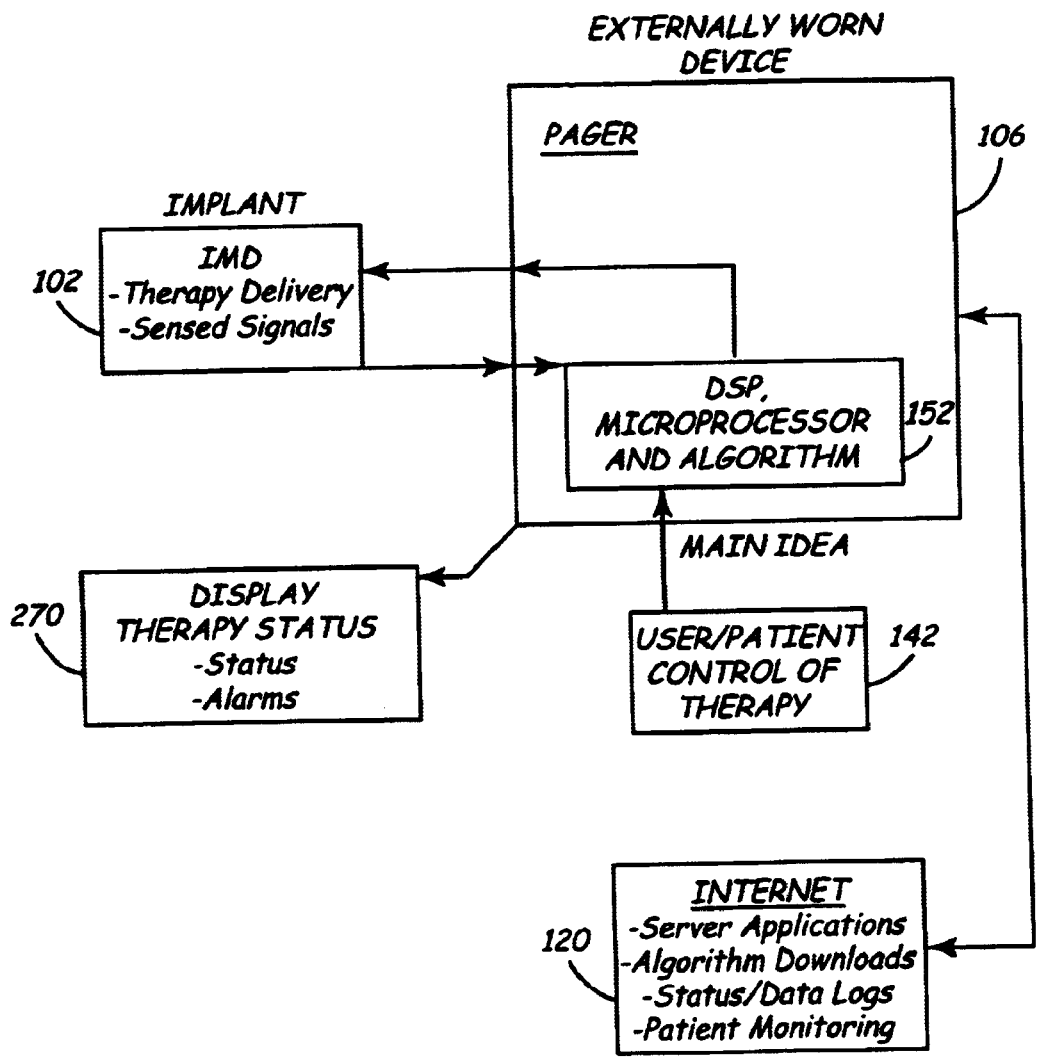
FIG. 5 is a schematic diagram of remote processing of an implantable medical device according to the present invention.

FIG. 5 is a schematic diagram of remote processing of an implantable medical device according to the present invention. As illustrated in FIGS. 1, 2, 4 and 5, the present invention enables information external to the patient, such as barometric pressure, temperature, patient body position and patient posture to be sensed through sensor 122. Transceiver device 106 performs calculations based on the external information from sensor 122, and/or additional information from implantable medical device 102 stored over a storage interval, such as diastolic, systolic and other parameters. The results of the calculations are then stored in transceiver device 106 or transmitted to implantable medical device 102 along link 108. As a result, the present invention enables data from both implantable medical device 102 and transceiver device 106 to be used to trigger high resolution storage or alarms based on hemodynamic parameters.

According to the present invention, an audible alarm from user interface 142 alerts patient 104 of hemodynamic parameters that are outside predetermined limits, and reasons or explanations for the alarm are provided at the display of interface 142, along with suggestions for returning the parameters back to acceptable levels through drug or diet adjustments, for example. Alternatively, the present invention enables data from status portion 270 of transceiver device 106 to be accessed by patient 104 and described to a physician or caretaker in conversations during adverse events. Furthermore, if more than one device is implanted within patient 104, such as implantable medical devices 102 and 132, data obtained by transceiver device 106 based on information received from implantable medical device 102 is used as feedback control information for implantable medical device 132. Implantable medical device 132 includes implanted or external drug pumps, for example, or other such device.

Transceiver device 106 accesses external information from sensor 122 to provide implantable medical device 102 directly with information for improved operation and/or additional functions. For example, the addition of the barometric pressure offset improves internal measured physiologic pressure resolution, and enables implantable medical device 102 to calculate real diastolic and systolic pressures which could then be used to determine pacing and drug therapies, while diagnostic information such as external heart rate variability measurements assist in guiding the pacing and drug therapies. In the addition, transceiver device accesses external information from sensor 122 for use in calculations relating to operation functions of implantable medical device 102, transmitting the results of the calculation to implantable medical device 102 or communication device 106, which then respond accordingly, or displays information or transmits an alarm to patient through interface 142.

Transceiver device 106 of the present invention also enables patient 104 to input information regarding the status of patient 104 that would assist one or both devices 102 and 106. For example, patient 106 informs transceiver device 106 when going to sleep, of measured body weight, when feeling ill or pre-syncopal, or when a syncopal episode has just taken place. Based on this patient input, transceiver device 106 either stores the information internally for later diagnostic use with implantable medical device 102, provides the information directly to implantable medical device 102 or to communication device 106, or performs a calculation using the patient input. Upon receipt, implantable medical device 102 then utilizes the patient input to perform calculations, to change a therapy, or to deliver a therapy. For example, according to the present invention, implantable medical device 102 increases a pacing rate as a result of information input by the patient at transceiver device 106.

Alternately, upon receiving information from patient 104 or sensor 122, transceiver device 106 can change monitoring modes. For example, transceiver device 106 changes the resolution of storage to enable more data to be recorded, or waits several minutes after receiving a message from patient 104 that patient 104 is going to sleep to initiate recording of baseline ECG or other patient parameters/signals. Likewise, a physician is able to remotely access the information input at transceiver device 106 by the patient through communication device 106.

The present invention enables system 100 to be automatically reprogrammed at a remote server, such as applications and data storage unit 114 (FIG. 1), or to be manually reprogrammed by patient 104, or remotely reprogrammed at remote location 116, or in a hospital, surgical, intensive care setting, by the physician, such as when the physician determines that the status of the patient has changed, resulting in a need for implantable medical device 102 to be reprogrammed, or in response to determining that there is a need to restart system 100 after having retrieved frozen or other data.

In addition, transceiver device 106 is used for communication to a box on a version of the same computer that handles programming via a telephonic link for programming during implant of device 102 and post implant. Transceiver device 106 enables automatically captured data, such as ECG signal, heart rate, pressure signal, pressure parameters, and/or patient activity to be retrieved from implantable medical device 102, increasing available memory space for storing additional parameters, such as heart rate variability requiring DSP algorithm processing, or for more frequent measurements for higher resolution. Transceiver device 106 becomes aware of the need to offload the implanted memory of stored data either on a periodic polling, or via an automatic or semi-automatic link, or interactively by patient 104 interactive control through interface 142. Transceiver device 106 either directly transmits the corresponding retrieved data to communication device 112, acts as an intermediate storage medium transmitting the retrieved data to remote locations 114 and 116 for data viewing and analysis, or performs calculations based on the retrieved data and transmits the results of the calculations to implantable medical device 102, to communication device 112, or to interface 142 for display or for transmitting an alarm signal to the patient.

It will be appreciated that the present invention can be utilized to monitor a patient and/or an implantable medical device implanted in a patient while in a hospital or intensive care setting by enabling information from the implantable medical device to be obtained wirelessly. Furthermore, according to the present invention, upon receipt of data from implantable medical device 102 and/or external information from sensor 122, and after performing the calculations using the received data and/or external information, transceiver device 106 either transmits the calculation results to implantable medical device 102 and/or communication device 112, transmits instructions associated with the calculation results to implantable medical device 102, or transmits a message or warning to the patient through interface 142. In response to receiving the calculation results or instructions, implantable medical device 102 either performs a therapy or calculation, or stores the calculation results or instruction for future reference. In the alternative, upon receipt, transceiver device 106 merely transmits the data and/or external information directly to communication device 112.

According to the present invention, transceiver device 106 warns patient 104 of device status issues through visual or audible feedback via status portion 270 of interface 142, and/or warns the physician or caretaker via communication device 112 or at the remote location. Important device status issues could include, for example, low battery and need for replacement, compromise in proper function of implantable medical device 102 due to system or subsystem failure, excess current amounts being utilized in a present mode of operation causing device 102 to go to low battery prematurely, heart rhythm or cardiac status is indicative of a major problem already ongoing or imminent, and so forth.

Finally, transceiver device 106 also incorporates other useful ancillary features, such as being a standard timepiece, reminding patient 104, either visually, audibly or both to take medicines, or of activity restrictions related to activities that the physician has instructed patient 104 not to engage in.

Figure 6:
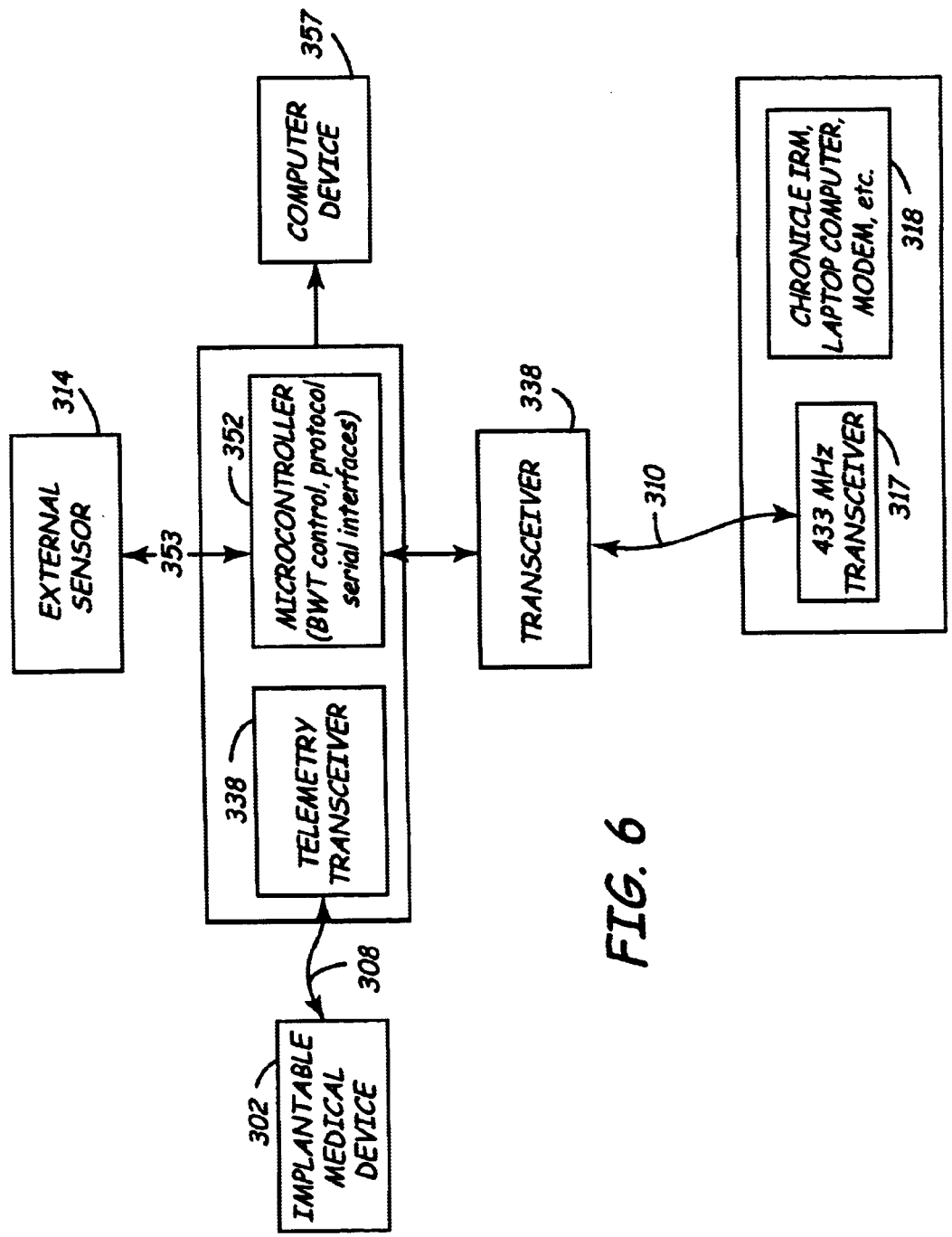
FIG. 6 is a schematic diagram of multi-directional data transmission using a transceiver device of the implantable medical device system of FIG. 1.

FIG. 6 is a schematic diagram of multi-directional data transmission using a transceiver device of the implantable medical device system of FIG. 1. As illustrated in FIG. 6, according to multi-directional data flow transmission of the present invention, an implantable medical device 302, such as the Medtronic Inc. Chronicle implantable hemodynamic monitor (IHM) for cardiac heart failure with a medium range telemetry link, for example, exchanges data with a transceiver device 306 along a link 308 between implantable medical device 302 and a transceiver 338. Transceiver device 306 includes a pager type device, for example, positioned within close proximity to, or worn on a belt of the patient, or a band-aid, wristwatch, or pendant type device positioned within close proximity of the patient, and so forth. Link 308 is a 3 Mhz body wave telemetry link, for example.

An external reference sensor 314 senses a parameter external to the patient, such as barometric pressure, and provides the external parameter to a microcontroller 352 of transceiver device 306 along a serial connection 353. It is understood that, while sensor 314 is described in FIG. 3 as being a barometric pressure sensor, according to the present invention, sensor 314 could sense any parameter external to the patient, such as, for example, temperature, position of the patients body, patient posture activity, and so forth.

Transceiver device 306 exchanges information with a communication device 312 along a wireless link 310 between a transceiver 339 of transceiver device 306 and a transceiver 317 located within communication device 312. Wireless link 310 is, for example, a 433 MHz radio frequency (RF) link having a range of approximately 30 to 70 meters. Communication device 312, which includes a base station, a monitor, a physician programmer, or other similar device, in turn exchanges information with a remote location, such as data storage unit 114 or health care provider 116 (FIG. 1) through a modem type device 318. Microcontroller 352 of transceiver device 306 is coupled, when necessary, such as during setup by a physician or nurse or during download of data, along a serial port 355 to a computer device 357, such as a laptop computer, palm pilot, or similar device having additional processing power, memory/data storage, and user interface.

According to the present invention, microprocessor 352 stores data and performs calculations based on information received from implantable medical device 302 or sensor 314, or both. For example, microprocessor 352 receives raw pressure data from sensor 314 and correlates atmospheric pressure, for example, to determine, using the correlated data and a predetermined algorithm, whether drug dosages should be increased or decreased, and transmits the information to implantable medical device 302, which, in the case where implantable medical device 302 is a drug delivery device, adjusts dosage amounts accordingly. In addition, microprocessor 352 transmits data to computer device 357 for use during set up, manufacture testing, and design debug procedures of implantable medical device 302, or for reference by the patient and/or physician.

In addition, according to the present invention, new therapy algorithms, or new enabling therapy features, can be remotely downloaded to the implantable medical device as they become available. Furthermore, the transceiver device can contain algorithms for various purposes, such as algorithms for altering control of the implantable medical device, for alarms to the patient based on data received from the implantable medical device, and so forth, which can be downloaded or altered remotely using the implantable medical device system of the present invention.

Figure 7:
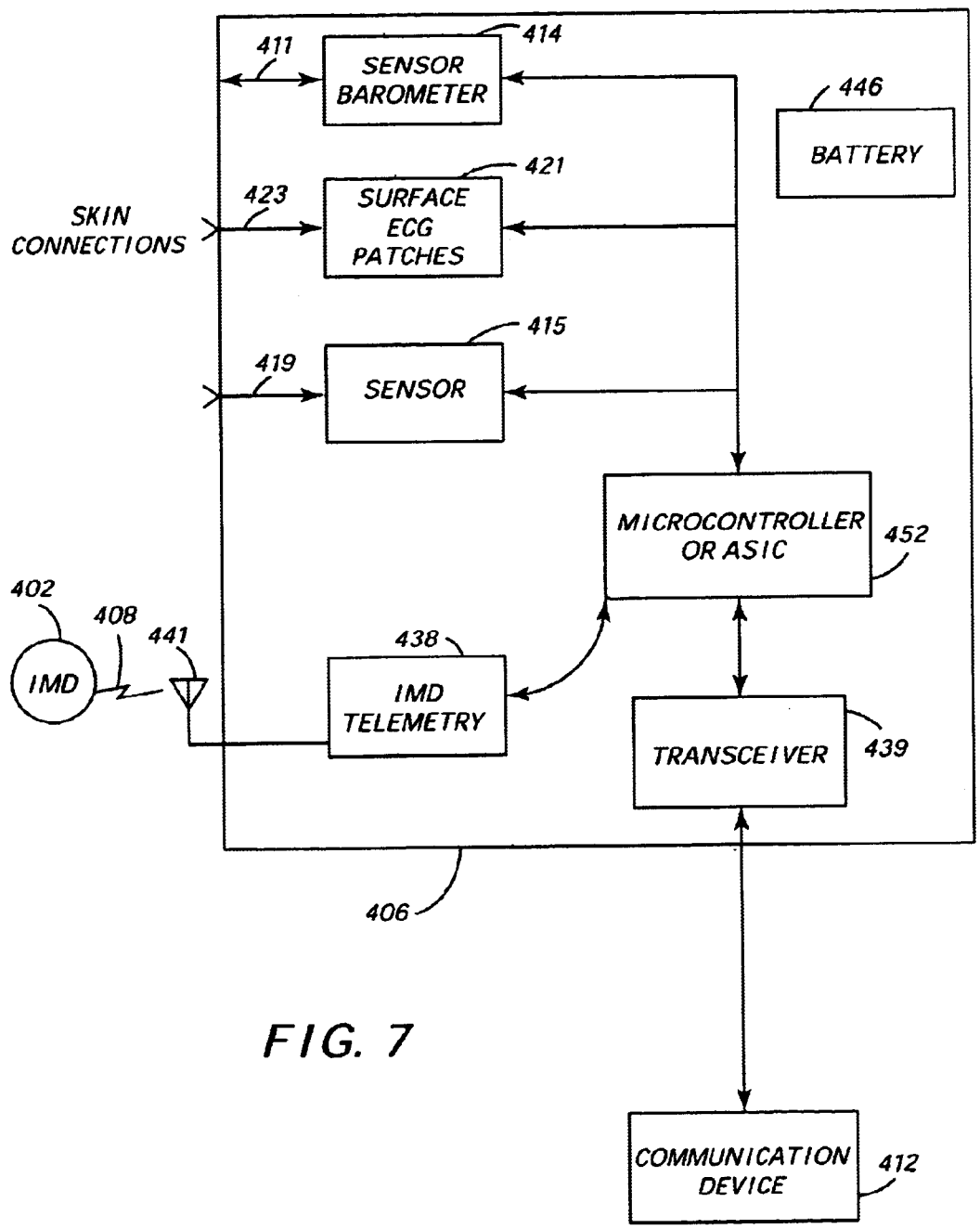
FIG. 7 is a schematic diagram of multi-directional data transmission using a transceiver device in the implantable medical device system of FIG. 1.

FIG. 7 is a schematic diagram of multi-directional data transmission using a transceiver device in the implantable medical device system of FIG. 1. According to a preferred embodiment of the present invention, a transceiver device 406 is coupled to an implantable medical device 402 along a link 408, such as a short range, low power telemetry link. Transceiver device 406 includes a band-aid type device, or peripheral memory patch, such as the peripheral memory patch describe in U.S. Pat. No. 6,200,265 issued to Walsh et al., and hereby incorporated herein by reference in its entirety. An external reference sensor 414 of transceiver device 406 is coupled along a port 411 to enable sensing of parameters by sensor 414 external to the patient, such as barometric pressure for example. In addition, external reference sensor 415 is coupled to the skin of the patient through a connector 419 to enable transceiver device 406 to sense other external, physiological or environmental parameters, such as temperature, physical activity, and so forth. Surface ECG patches 421 are also coupled to the patient's skin through a connector 423 to enable transceiver device 406 to collect information for forming an electrocardiogram (ECG) of the patient. Skin connectors 419 and 423 include gel patches, micro needles or any other device for connecting to the patient's skin. Transceiver device 406 exchanges information along link 408 with implantable medical device 402 through an implantable medical device telemetry unit or transceiver 438 and an antenna 441. Information is exchanged between a transceiver 439, such as a UHF transceiver, for example, and a long range source or communication device 412, which includes a monitor or physician programmer, for example, along a long range telemetry link 410. Finally, a rechargeable or replaceable battery 446 is positioned provides energy to power transceiver device 406.

As illustrated in FIG. 7, a microcontroller 452 receives and stores or manipulates information from sensors 414 and 415, patches 421 and transceivers 438 and 439, and transmits received, stored, or manipulated data to implantable medical device 402 and/or long range source 412 as described above. For example, transceiver device 406 receives a signal from patches 421 and provides ECG signals corresponding to the patient to long-range source 412 for reference by a physician or the patient. Barometric data from sensor 414 provides a barometric reference for calibrating an implanted cardiac pressure sensor, which could then be utilized for real-time therapy decisions.

Figure 8:
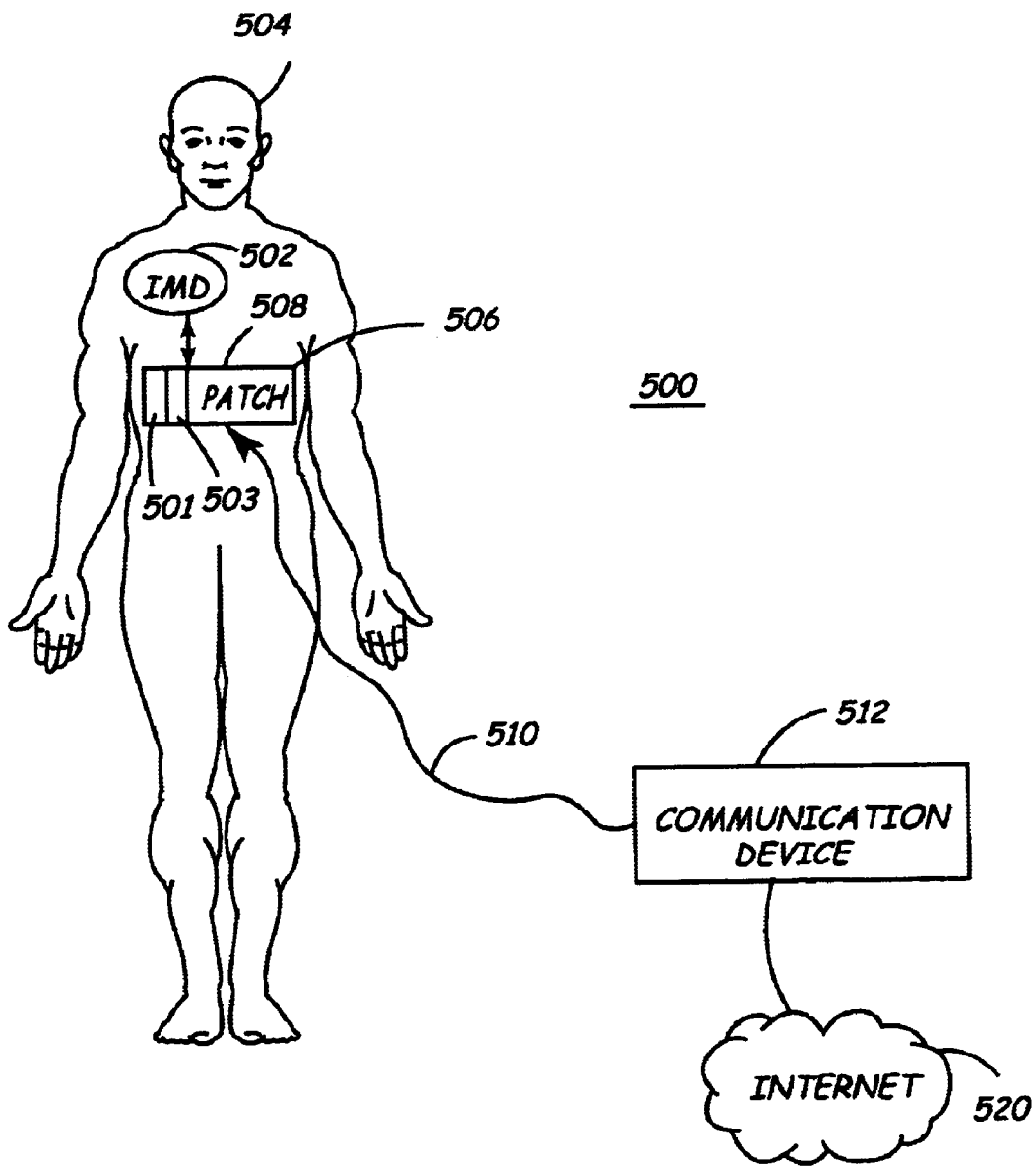
FIG. 8 is a schematic diagram of multi-directional data transmission using a transceiver device in the implantable medical device system of FIG. 1.

FIG. 8 is a schematic diagram of multi-directional data transmission using a transceiver device in the implantable medical device system of FIG. 1. As illustrated in FIG. 8, an implantable medical device system 500 according to the present invention is similar to those previously described above, and includes an implanted medical device 502 implanted within a patient 504, and a transceiver device 506, such as a pager, band-aid, wristwatch or pendant type device positioned within close proximity to implantable medical device 502 to be bi-directionally coupled with implantable medical device 502 along a link 508. In addition, transceiver device 506 is coupled along a link 510 to a communication device 512, such as a base station, monitor, or physician programmer, for example, which in turn is coupled to the Internet 520 and can thus be accessed at a remote location (not shown). Transceiver device 506 utilizes disposable (one-time use), replaceable, or rechargeable batteries (not shown).

According to a preferred embodiment of the present invention, transceiver device 506 includes a converter unit 501 for converting between various different implantable medical device telemetry formats, each telemetry format having one or more unique features, such as carrier frequency, modulation method, and/or data protocol. In this way, transceiver device 506 functions as a telemetry repeater of sorts, enabling transmission of data between implantable medical device 502 and transceiver device 506 in multiple telemetry formats. For example, prior to transmitting the data to communication device 512, converter unit 501 converts one of a telemetry range, carrier frequency, modulation method, and/or data protocol associated with information received from implantable medical device 502 to a corresponding telemetry range, carrier frequency, modulation method, and/or data protocol associated with communication device 512. In the same way, prior to transmitting data to implantable medical device 502, converter unit 501 converts one of a telemetry range, carrier frequency, modulation method, and/or data protocol associated with information received from communication device 502 to a corresponding telemetry range, carrier frequency, modulation method, and/or data protocol associated with implantable medical device 502. As a result, the present invention eliminates the need for telemetry cables between communication device 512 and transceiver device 506 so that patient 504 is free to go about daily activities while a large data file is uploaded, or during programming or testing of implantable medical device 502. In addition, by eliminating the need for a hard wire connection between transceiver device 506 and communication device 512, the present invention enables transceiver device 506 to more easily be entered within a sterile field during an implant procedure, for example, and enables wireless bedside monitoring in a hospital or intensive care setting.

Converter unit 502 periodically, or at certain physiological or other events, gathers data from implantable medical device 502 and transmits the gathered data or commands to second implantable medical device 132 (FIG. 2). Transceiver device 506 also includes a memory 503 for storing information regarding implantable medical device 502, or conditions of patient 504 over time, so that patient 504 would activate transceiver device 506 prior to a follow-up visit and interrogate data to be turned into the physician or health care provider. For example, transceiver device 506 would be turned over to the health care provider and read into the physician's programmer, via a PCMCIA or serial interface, or could also reach the physician via a remote Internet connection. For surgical procedures, a short range implantable medical device telemetry is converted by converter unit 501 to a longer range implantable medical device telemetry, such as a UHF link, for example, enabling the physician programmer to be kept outside the sterile field. In this way, converter unit 501 allows a physician programmer to communicate with implantable medical devices 506 and 132, for example, by enabling a physician programmer related to one implantable medical device to communicate with a second implantable medical device different from the first device, removing the cost and complexity from a specific programmer or having to utilize separate programmers, while providing the physician the ability to communicate with multiple implantable medical devices (telemetry types) in an emergency room setting or in a rural clinic, and to store information from a broad range of devices.

It is understood that while the communication device of the present invention has been described above as being base station, a monitor, a physician programmer, or other similar device, communication device also includes an Internet device, with or without user controls, that transmits data remotely, such as to a physician programmer at a remote location, or to an Internet web page.

The preceding specific embodiments are illustrative of the practice of the invention. It is to be understood, therefore, that other expedients known to those of skill in the art or disclosed herein may be employed. In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures. It is therefore to be understood, that within the scope of the appended claims, the invention may be practiced otherwise than as specifically described without actually departing from the spirit and scope of the present invention.

What is claimed is:

1. An implantable medical device system, comprising:
an implantable medical device for implantation within a patient, the implantable medical device monitoring physiologic conditions of the patient, and/or delivering a therapy in response to the physiologic conditions;
a transceiver device, coupled to the implantable medical device along a wireless link, exchanging data with the patient, between the patient and the implantable medical device, and between a remote location and the implantable medical device; and
a communication device, coupled to the transceiver device along a wireless link, exchanging data with the transceiver device, with the implantable medical device through the transceiver device, and between the transceiver device and the remote location, wherein the implantable medical device system enables bi-directional data transfer between the patient, the implantable medical device, the transceiver device, the communication device, and the remote location, wherein the transceiver device triggers the implantable medical device to change from a normal state, in which implantable medical device gathers data at a first rate and performs a relatively high amount of averaging, to a second state in which the amount and resolution of data is increased so that an increased resolution of data is obtained and stored in transceiver device in response to an input to the transceiver by the patient.

2. The implantable medical device system of claim 1, the system further comprising a converter unit converting transmission of the data between the implantable medical device, the transceiver device, and the communication device from a first telemetry format to a second telemetry format.

3. The implantable medical device system of claim 1, further comprising a direct interface coupling the transceiver device to an external device to enable direct downloading of the data and configuration/setup information to the external device, and connection to user interface devices.

4. The implantable medical device system of claim 1, wherein the transceiver device includes one of a pager type device, a band-aid, a wristwatch, and a pendant type device.

5. The implantable medical device system of claim 1, further comprising an external reference sensor sensing a parameter external to the patient, the transceiver device receiving the sensed parameter from the external reference sensor and/or receiving data from the implantable medical device, wherein the transceiver device either directly transmits the sensed parameter and/or the data received from the implantable medical device to the communication device, stores the sensed parameter and/or the data received from the implantable medical device for subsequent transmission to the remote location, performs calculations based on the sensed parameter and/or the data received from the implantable medical device and transmits results of the calculations to the implantable medical device or the communication device, or transmits a display or an alarm signal corresponding to results of the calculation.

6. The implantable medical device system of claim 1, further comprising a user interface enabling information to be exchanged between the transceiver device and the patient, between the implantable medical device and the patient through the transceiver device, and between the patient and the remote location.

7. The implantable medical device system of claim 1, wherein data received by transceiver device is used as feedback control information for a second implantable medical device for implantation within the patient.

8. The implantable medical device system of claim 1, further comprising a removable memory storing information received directly from the transceiver device and received from the implantable medical device through the transceiver device.

9. The implantable medical device system of claim 1, wherein the communication device is one of a base station, a monitor, a physician programmer, and an internet device.

10. The implantable medical device system of claim 1, wherein the system transmits a warning in response to status issues corresponding to the implantable medical device through one of the transceiver device, the communication device, and the remote location.

11. The implantable medical device system of claim 1, wherein the transceiver device reminds the patient to take medications, and/or reminds the patient of activity restrictions.

12. The implantable medical device system of claim 1, wherein the implantable medical device system is reprogrammed directly by the patient or remotely at one of the remote location and the communication device.

13. An implantable medical device system, comprising:
   an implantable medical device for implantation within a patient, the implantable medical device monitoring physiologic conditions of the patient, and/or delivering a therapy in response to the physiological conditions;
   a transceiver device, coupled to the implantable medical device along a wireless link, exchanging data with the patient, between the patient and the implantable medical device, and between a remote location and the implantable medical device;
   communication device, coupled to the transceiver device along a wireless link, exchanging data with the transceiver device, with the implantable medical device through the transceiver device, and between the transceiver device and the remote location, wherein the implantable medical device system enables bi-directional data transfer between the patient, the implantable medical device, the transceiver device, the communication device, and the remote location; and
   a user inferface enabling information to be exchanged between the transceiver device and the patient, between the implantable medical device and the patient through the transceiver device, and between the patient and the remote location, wherein the user interface comprises:
      a patient physiologic parameter portion displaying the physiologic conditions of the patient;
      a daily activity diary portion enabling the patient to input activities to the transceiver device;
      a medication reminder portion displaying medication reminders in response to a request received from the implantable medical device and in response to data processed by the implantable medical device and the transceiver device;
      an event storage portion storing information, including the input activities and physiologic signals associated with the patient, processing the information, and acquiring high resolution activity in response to the information;
      a send message portion storing messages transmitted between the remote location and the transceiver device and/or the patient;
      a status portion adjusting and displaying battery status, therapy status, and settings of the transceiver device; and
      a receive message portion receiving messages transmitted between the remote location and the transceiver device and/or the patient, the received messages including one of automated information, adjusting parameter and output of the implantable medical device, and manual information, input directly at the transceiver device.

14. A patient wearable transceiver device exchanging data with an implantable medical device for implantation within a patient and a communication device, comprising:
   means for receiving information from the implantable medical device;
   means for exchanging data between the patient, the implantable medical device, the communication device, and a remote location; and
   means for processing the data exchanged to enable bi-directional data transfer between the patient, the implantable medical device, the transceiver device, and the remote location, wherein the transceiver device triggers the medical device gathers data at a first rate and performs a relatively high amount of averaging, to a second state in which the amount and resolution of data is increased so that an increased resolution of data is obtained and stored in transceiver device in response to an input to the transceiver by the patient.

15. The device of claim 14, further comprising means for converting data exchanged between the implantable medical device, the transceiver device, and the communication device from a first telemetry format to a second telemetry format.

16. The device of claim 14, further comprising direct interface means coupling the transceiver device to an external device to enable direct downloading of the data and configuration/Setup information to the external device, and connection to user interface devices.

17. The device of claim 14, wherein the transceiver device includes one of a pager type device, a band-aid, a wristwatch, and a pendant type device.

18. The device of claim 14, further comprising a sensing means for sensing a parameter external to the patient, the transceiver device receiving the sensed parameter from the sensing means and/or receiving data from the implantable medical device, wherein the transceiver device either directly transmits the sensed parameter and/or the data received from the implantable medical device to the communication device, stores the sensed parameter and/or the data received from the implantable medical device for subsequent transmission to the remote location, performs calculations based on the sensed parameter and/or the data received from the implantable medical device and transmits results of the calculations to the Implantable medical device or the communication device, or transmits a display or an alarm signal corresponding to results of the calculation.

19. The device of claim 14, further comprising a user interface for enabling information to be exchanged between the transceiver device and the patient, between the implantable medical device and the patient through the transceiver device, and between the patient and the remote location.

20. The device of claim 14, wherein data received by transceiver device is used as feedback control information for a second implantable medical device for implantation within the patient.

21. The device of claim 14, further comprising means for storing information received directly from the transceiver device and received from the implantable medical device through the transceiver device, the means for storing information being removable from the device.

22. The device of claim 14, further comprising means for transmitting a warning in response to status issues corresponding to the implantable medical device through one of the transceiver device, the communication device, and the remote location.

23. The device of claim 14, further comprising means for reminding the patient to take medications and/or of activity restrictions.

24. A patient wearable transceiver device exchanging data with an implantable medical device for implantation within a patient and a communication device, comprising:
  means for receiving information from the implantable medical device;
  means for exchanging data between the patient, the implantable medical device, the communication device, and a remote location;
  means for processing data exchange to enable bi-directional data transfer between the patient, the implantable medical device, the transceiver device, and the remote location; and
  a user interface means for enabling information to be exchanged between the transceiver device and the patient, between the implantable medical device and the patient through the transceiver device, and between the patient and the remote location, wherein the user interface means comprises:
    means for displaying the physiologic conditions of the patient;
    means for enabling the patient to input activities to the transceiver device;
    means for displaying medication reminders in response to a request received from the implantable medical device and in response to data processed by the implantable medical device and the transceiver device;
    means for storing information, including the input activities and physiologic signals associated with the patient, processing the information, and acquiring high resolution activity in response to the information;
    means for storing messages transmitted between the remote location and the transceiver device and/or the patient;
    means for adjuring and displaying battery status, therapy status, and settings of the transceiver device; and
  means for receiving messages transmitted between the remote location and the transceiver device and/or the patient the received messages including one of automated information, adjusting parameters and output of the implantable medical device, and manual information, input directly at the transceiver device.

25. An implantable medical device system, comprising:
  an implantable medical device for implantation within a patient, the implantable medical device monitoring physiologic conditions of the patient, and/or delivering a therapy in response to physiologic conditions;
  a transceiver device, coupled to the implantable medical device along a wireless link, exchanging data with the patient, between the patient and the implantable medical device, and between a remote location and the implantable medical device;
  a communication device, coupled to the transceiver device along a, wireless link, exchanging data with the transceiver device and with the implantable medical device through the transceiver device, and exchanging data between the transceiver device and the remote location;
  a converter unit converting transmission of the data between the implantable medical device, the transceiver device, and the communication device from a first telemetry format to a second telemetry format;
  a direct interface coupling the transceiver device to an external device to enable direct downloading of the data and configuration/Setup information to the external device, and connection to user interface devices;
  an external reference sensor sensing a parameter external to the patient, the transceiver device receiving the sensed parameter from the external reference sensor and/or receiving data from the implantable medical device; and
  a user interface enabling information to be exchanged between the transceiver device and the patient, between the implantable medical device and the patient through the transceiver device, and between the patient and the remote location.

26. The implantable medical device system of claim 25, wherein the user interface enable information to be exchanged between the patient and the communication device.

27. The implantable medical device system of claim 25, wherein the transceiver device either directly transmits the sensed parameter and/or the data received from the implantable medical device to the communication device, stores the sensed parameter and/or the data received from the implantable medical device for subsequent transmission to the remote location, performs calculations based on the sensed parameter and/or the data received from the implantable medical device and transmits results of the calculations to the implantable medical device or the communication device, or transmits a display or an alarm signal corresponding to results of the calculation.

28. The implantable medical device system of claim 27, wherein the transceiver device includes one of a pager type device, a band-aid, a wristwatch, and a pendant type device.

29. The implantable medical device system of claim 28, wherein the user interface comprises:
- a patient physiologic parameter portion displaying the physiologic conditions of the patient;
- a daily activity diary portion enabling the patient to input activities to the transceiver device;
- a medication reminder portion displaying medication reminders in response to a request received from the implantable medical device and in response to data processed by the implantable medical device and the transceiver device;
- an event storage portion storing information, including the input activities and physiologic signals associated with the patient, processing the information, and acquiring high resolution activity in response to the information;
- a send message portion storing messages transmitted between the remote location and the transceiver device and/or the patient;
- a status portion adjusting and displaying battery status, therapy status, and settings of the transceiver device; and
- a receive message portion receiving messages transmitted between the remote location and the transceiver device and/or the patient, the received messages including one of automated information, adjusting parameters and output of the implantable medical device, and manual information, input directly at the transceiver device.

30. The implantable medical device system of claim 29, Wherein data received by transceiver device is used as feedback control information for a second implantable medical device for implantation within the patient.

31. The implantable medical device system of claim 30, further comprising a removable memory storing information received directly from the transceiver device and received from the implantable medical device through the transceiver device.

32. The implantable medical device system of claim 31, wherein the transceiver device triggers the implantabie medical device to change from a normal state, in which implantable medical device gathers data at a first rate and performs a relatively high amount of averaging, to a second state in which the amount and resolution of data is increased so that an increased resolution of data is obtained and stored in transceiver device in response to an input to the transceiver by the patient.

33. The implantable medical device system of claim 32, wherein the communication device is one of a base station, a monitor, a physician programmer, and an Internet device.

34. The implantable medical device system of claim 33, wherein the system transmits a warning in response to status issues corresponding to the implantable medical device through one of the transceiver device, the communication device, and the remote location.

35. The implantable medical device system of claim 34, wherein the transceiver device reminds the patient to take medications, and/or reminds the patient of activity restrictions.

36. The implantable medical device system of claim 35, wherein the implantable medical device system is reprogrammed directly by the patient or remotely at one of the remote location and the communication device.

37. An implantable medical device system, comprising;
- an implantable medical device for implantation within a patient, the implantable medical device monitoring physiologic conditions of the patient, and/or delivering a therapy in response to the physiologic conditions;
- a transceiver device, coupled to the implantable medical device along a wireless link, exchanging data with the patient, between the patient and the implantable medical device, and between a remote location and the implantable medical device;
- a communication device, coupled to the transceiver device along a wireless link, exchanging data with the transceiver device, with the implantable medical device through the transceiver device, and between the transceiver device and the remote location, wherein the implantabie medical device system enables bi-directional data transfer between the patient, the implantable medical device, the transceiver device, the communication device, and the remote location;
- a direct interface coupling the transceiver device to an external device to enable direct downloading of the data and configuration/setup information to the external device, and connection to user interface devices; and
- an external reference sensor sensing a parameter external to the patient, the transceiver device receiving the sensed parameter from the external reference sensor and/or receiving data from the implantable medical device.

* * * * *

UNITED STATES PATENT AND TRADEMARK OFFICE
CERTIFICATE OF CORRECTION

PATENT NO. : 6,738,671 B2
DATED : May 18, 2004
INVENTOR(S) : Mark A. Christopherson et al.

It is certified that error appears in the above-identified patent and that said Letters Patent is hereby corrected as shown below:

Title page,
Item [75], Inventor, delete "Christophersom" replace with -- Christopherson --.

Column 15,
Line 66, delete "communication device", replace with -- a communication device --.

Column 16,
Line 52, delete "triggers the medical device gathers data" replace with -- triggers the implantable medical device to change from a normal state, in which implantable medical device gathers data --.
Line 66, delete "configuration/Setup" replace with -- configuration/setup --.

Column 17,
Line 15, delete "the Implantable" replace with -- the implantable --.

Column 18,
Line 8, delete "for adjuring", replace with -- for adjusting --.
Line 13, delete "the patient the received", replace with -- the patient, the received --.
Line 28, delete "along a, wireless", replace with -- along a wireless --.
Line 40, delete "configuration/Setup", replace with -- configuration/setup --.

Column 19,
Line 34, delete "Wherein", replace with -- wherein --.

Column 20,
Line 5, delete "Internet", replace with -- internet --.

Signed and Sealed this

Eighteenth Day of January, 2005

JON W. DUDAS
*Director of the United States Patent and Trademark Office*